(12) United States Patent
Tang et al.

(10) Patent No.: US 11,596,643 B2
(45) Date of Patent: Mar. 7, 2023

(54) PECTIN-ADRIAMYCIN CONJUGATE AS WELL AS PREPARATION METHOD AND USE THEREOF

(71) Applicant: Sichuan Yingrui Pharmaceutical Technology Company, Sichuan (CN)

(72) Inventors: Xiaohai Tang, Sichuan (CN); Cheng Zeng, Sichuan (CN); Yuanfang Huang, Sichuan (CN)

(73) Assignee: SICHUAN YINGRUI PHARMACEUTICAL TECHNOLOGY COMPANY, Sichuan (CN)

( * ) Notice: Subject to any disclaimer, the term of this patent is extended or adjusted under 35 U.S.C. 154(b) by 0 days.

(21) Appl. No.: 16/636,343

(22) PCT Filed: Jun. 18, 2019

(86) PCT No.: PCT/CN2019/091627
§ 371 (c)(1),
(2) Date: Feb. 4, 2020

(87) PCT Pub. No.: WO2020/252648
PCT Pub. Date: Dec. 24, 2020

(65) Prior Publication Data
US 2022/0110957 A1   Apr. 14, 2022

(51) Int. Cl.
*A61K 31/704*   (2006.01)
*A61K 47/61*   (2017.01)
*A61P 35/00*   (2006.01)

(52) U.S. Cl.
CPC ............ *A61K 31/704* (2013.01); *A61K 47/61* (2017.08); *A61P 35/00* (2018.01)

(58) Field of Classification Search
CPC ........ A61K 31/704; A61K 47/61; A61P 35/00
See application file for complete search history.

(56) References Cited

FOREIGN PATENT DOCUMENTS

| CN | 101045163 | * | 3/2011 | ............. A61K 47/48 |
|----|-----------|---|--------|-------------------------|
| CN | 105342850 | A |  2/2016 |                         |

OTHER PUBLICATIONS

CN101045163 (machine translation provided; translation done on Jan. 18, 2022).*
Bonzi (Bioconjugate Chemistry; 2015, 26, 489-501).*

* cited by examiner

*Primary Examiner* — Pancham Bakshi
(74) *Attorney, Agent, or Firm* — Yue (Robert) Xu; Apex Attorneys at Law, LLP

(57) ABSTRACT

The disclosure relates to a pectin-adriamycin conjugate, and discloses a preparation method and use of the conjugate above. The pectin-adriamycin conjugate of the disclosure has a completely new chemical structure and can be accumulated in a malignant tumor tissue for a long time with a high concentration in a targeting manner so as to achieve the purposes of enhancing effects and reducing toxicity, and the indications are chemotherapies of various solid malignant tumors.

1 Claim, 5 Drawing Sheets

PECTIN-ADRIAMYCIN CONJUGATE AS WELL AS PREPARATION METHOD AND USE THEREOF

The present application is a U.S. National Phase application based upon PCT Application Serial No. PCT/CN2019/091627 submitted on Jun. 18, 2019 with the invention name of "PECTIN-ADRIAMYCIN CONJUGATE AS WELL AS PREPARATION METHOD AND USE THEREOF," the entire disclosures of which are incorporated herein by reference.

TECHNICAL FIELD

This disclosure relates to the field of pharmacy, and in particularly, to a pectin-adriamycin conjugate as well as a preparation method and use thereof.

BACKGROUND

A "pectin-adriamycin conjugate" targeted drug delivery system (PAC) is based on a great amount of preliminary work and literature studies, in which pectin is selected as a carrier for polymeric anti-cancer prodrugs, and the structure of pectin is modified so that it can be covalently bonded to a polypeptide-adriamycin to form a water-soluble pectin-adriamycin conjugate with a high drug loading.

PAC is a polymeric conjugate having a particle diameter of about 200 nm, and some drugs that enter the circulatory system after injection can be accumulated in a tumor tissue by use of the enhanced permeability and retention effect (EPR) of the tumor tissue to the macromolecular substance so as to achieve the purpose of passive targeting. PAC is gradually phagocytized by tumor cells in the tumor tissue and hydrolyzed in lysosomes to release adriamycin so as to exert a tumor-killing effect. The existing pectin-adriamycin conjugates are all formed by directly bonding pectin to adriamycin via an amide bond or an acylhydrazone bond, and thus are hardly soluble in water, and must be prepared into a nano-suspension or lyophilized powder for injection, which can only be locally administrated; if being systemically administrated, they are easily phagocytized by the reticuloendothelial system, have a limited targeting effect, cannot be accumulated in a malignant tumor tissue for a long time with a high concentration, and thus have a an inefficient anti-tumor effect.

SUMMARY

In view of the disadvantages in the prior art, an object of this disclosure is to provide a pectin-adriamycin conjugate that can be accumulated in a malignant tumor tissue for a long time with a high concentration in a targeting manner so as to achieve the purposes of enhancing effects and reducing toxicity. The disclosure also provides a preparation method for the pectin-adriamycin conjugate as described above.

In order to achieve the above objects, the technical solution of the disclosure is a pectin-adriamycin conjugate having a structure shown in formula (I):

a-b-c-d-e  (I), wherein a is pectin or a modified pectin, b is PEGn (PEGn is polyethylene glycol), c is an enzymatic cleaving group, a polypeptide or a polypeptide derivative, d is a self-degrading group, and e is adriamycin.

The pectin is a polygalacturonic acid ester-free pectin, the molecular weight of a is 1-4 KD and, more preferably, the content of galacturonic acid in the polygalacturonic ester-free pectin is 95% or more. Further, the modified pectin is obtained by reacting a carbonyl group of a polygalacturonic acid ester-free pectin with a hydroxyl-substituted $C_2$-$C_4$ alkylamine to form an amide, which is further activated to become a pectin carbonic ester;

Further, in formula (I), b is PEGn n is an integer of 1-20, c is a dipeptide, a dipeptide derivative, a tripeptide, a tripeptide derivative, a tetrapeptide or a tetrapeptide derivative; preferably, n is an integer of 6-12, and c is val-ala.

Further, d is p-aminobenzyloxycarbonyl (PABC).

The disclosure also discloses a preparation method for the pectin-adriamycin conjugate as described above, in which a compound of formula (13) is reacted with a compound of formula (9) in presence of an alkaline reagent,

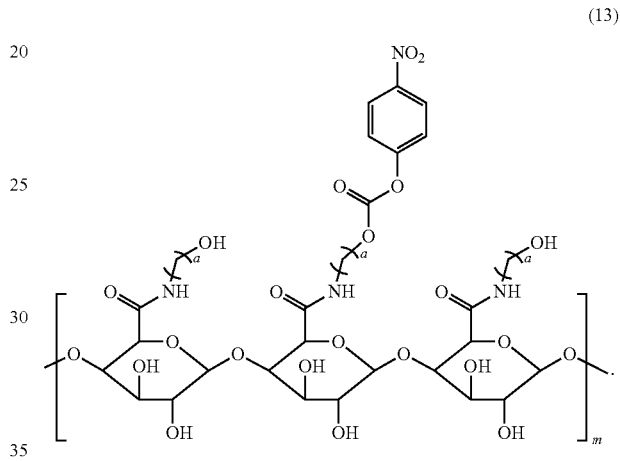

(13)

In formula (13), a is an integer selected from 2-4, and m is 1-60; the compound of formula (9) is b-c-d-ADM, wherein ADM is adriamycin, b is PEGn, and c is a polypeptide; preferably, c is a dipeptide, a dipeptide derivative, a tripeptide, a tripeptide derivative, a tetrapeptide or a tetrapeptide derivative; preferably, n is an integer of 6-12; preferably, c is val-ala; preferably, d is PABC; PEGn is polyethylene glycol, and n represents a degree of polymerization.

Further, a preparation method of the compound of formula (13) is as follows: a carboxyl group of pectin is condensed with an alcohol (methnol) to obtain an esterified pectin, the esterified pectin is reacted with a hydroxyl-substituted $C_2$-$C_4$ alkylamine to generate an amide, which then is reacted with di(4-nitrophenyl)carbonate to obtain the compound of formula (13).

Further, a preparation method of the compound of formula (9) is as follows: a compound of formula (5) is reacted with adriamycin in presence of an alkaline reagent to obtain a compound of formula (6), the compound of formula (6) is subjected to de-protection in presence of piperidine to obtain a compound of formula (7), the compound of formula (7) is reacted with $R_1$-b-COOH to obtain a compound of formula (8), and then the compound of formula (8) is subjected to de-protection in presence of piperidine to obtain the compound of formula (9); the compound of formula (5) is $R_1$-c-PABC, the compound of formula (6) is $R_1$-c-PABC-e, the compound of formula (7) is c-PABC-e, and the compound of formula (8) is $R_1$-b-c-PABC-e, wherein $R_1$ is a protecting group; preferably, $R_1$ is fluorenylmethoxycarbonyl (Fmoc).

Further, a preparation method of the compound of formula (5) is as follows: a compound of formula (3) is reacted with p-aminobenzyl alcohol in presence of an acid binding agent to obtain a compound of formula (4), and then the compound of formula (4) is reacted with di(4-nitrophenyl) carbonate in presence of an alkaline reagent to obtain the compound of formula (5); the compound of formula (3) is $R_1$-c-OH, and the compound of formula (4) is $R_1$-c-PABOH, wherein PABOH is 4-(hydroxymethyl)phenylamino.

Further, a preparation method of the compound of formula (3) is as follows: a compound of formula (1) is reacted in presence of NHS and DCC to obtain a compound of formula (2), and then the compound of formula (2) is reacted with an amino acid in presence of an alkaline reagent to obtain the compound of formula (3); the compound of formula (1) is $R_1$-$c_1$-OH, and the compound of formula (2) is $R_1$-$c_1$-OSu, wherein $c_1$ is an amino acid; preferably, $c_1$ is val.

The disclosure also discloses use of the pectin-adriamycin conjugate as described above in preparation of a medicament for treating cancers.

The advantages and effects of the invention:

The pectin-adriamycin conjugate of this disclosure has a completely new chemical structure and can be accumulated in a malignant tumor tissue for a long time with a high concentration in a targeting manner to achieve the purposes of enhancing effects and reducing toxicity, and the indications are chemotherapies of various solid malignant tumors.

DETAILED DESCRIPTION

Figure 1:
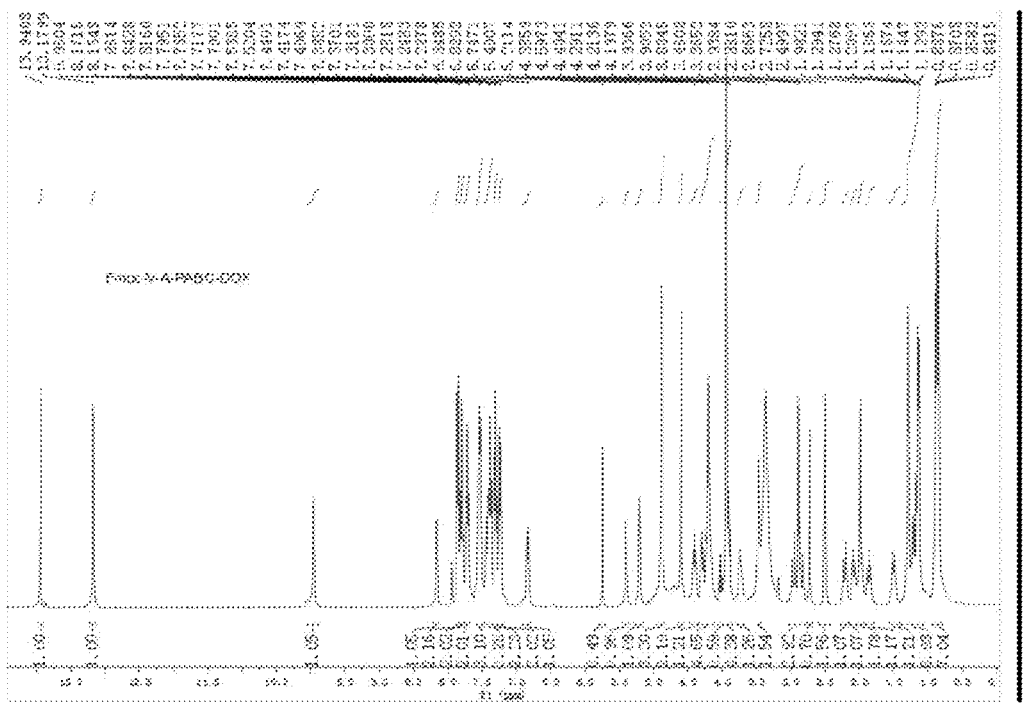
FIG. 1 is the $^1$H NMR spectrum of Compound 6.
Figure 2:
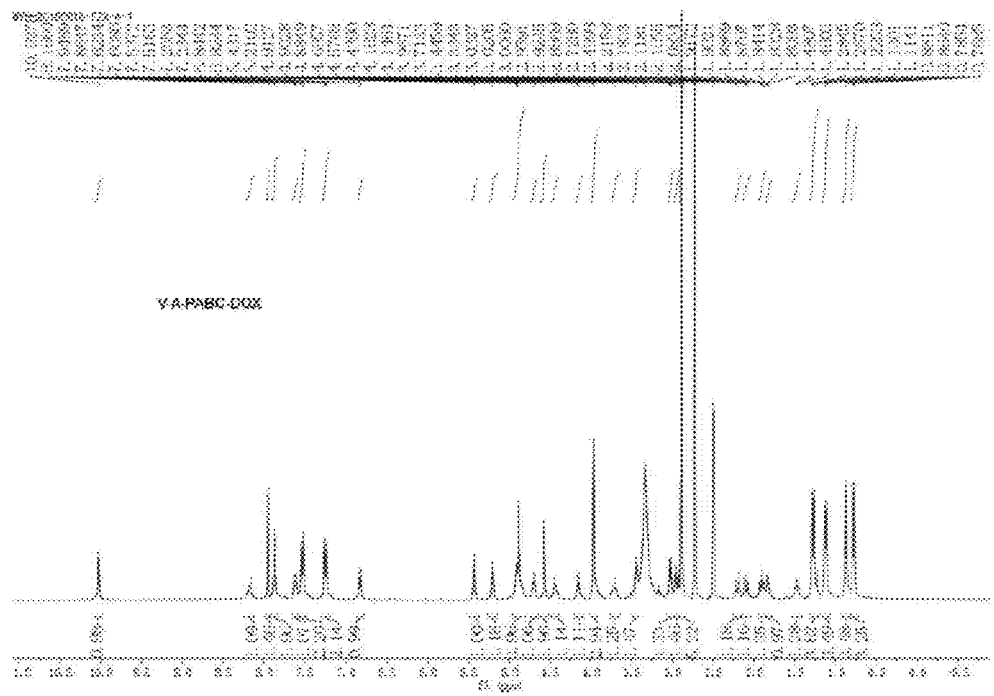
FIG. 2 is the $^1$H NMR spectrum of Compound 7.
Figure 3:
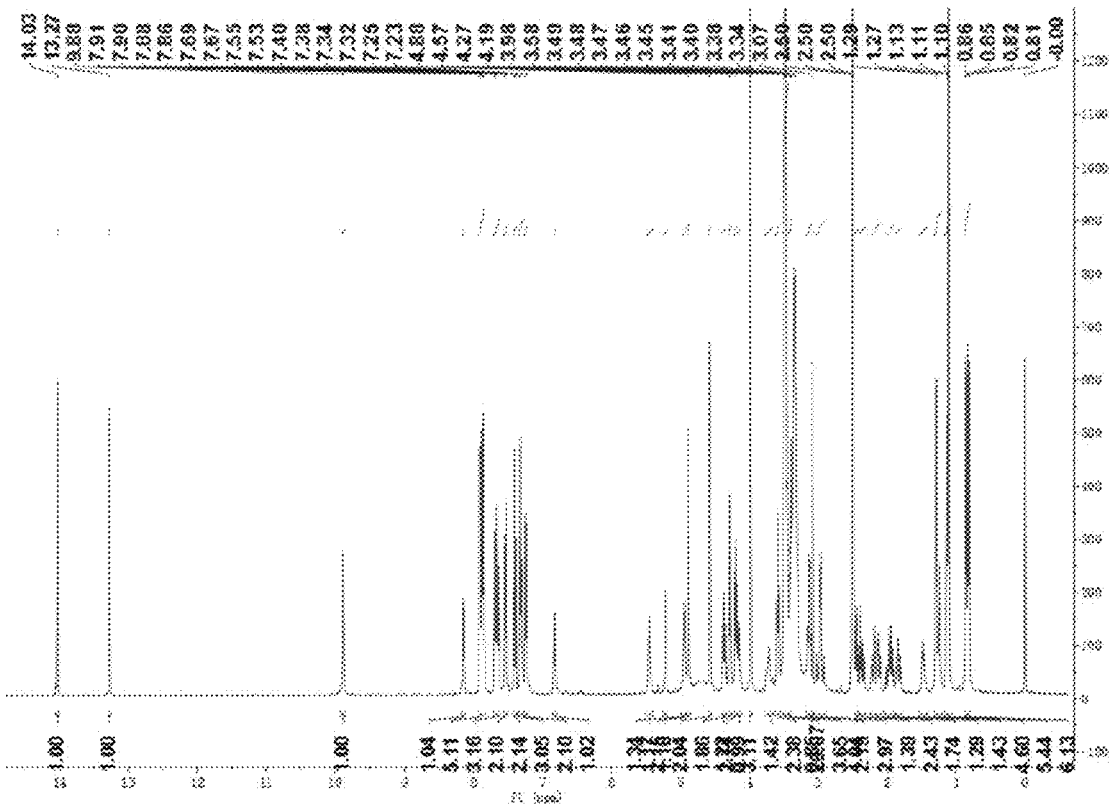
FIG. 3 is the $^1$H NMR spectrum of Compound 8.
Figure 4:
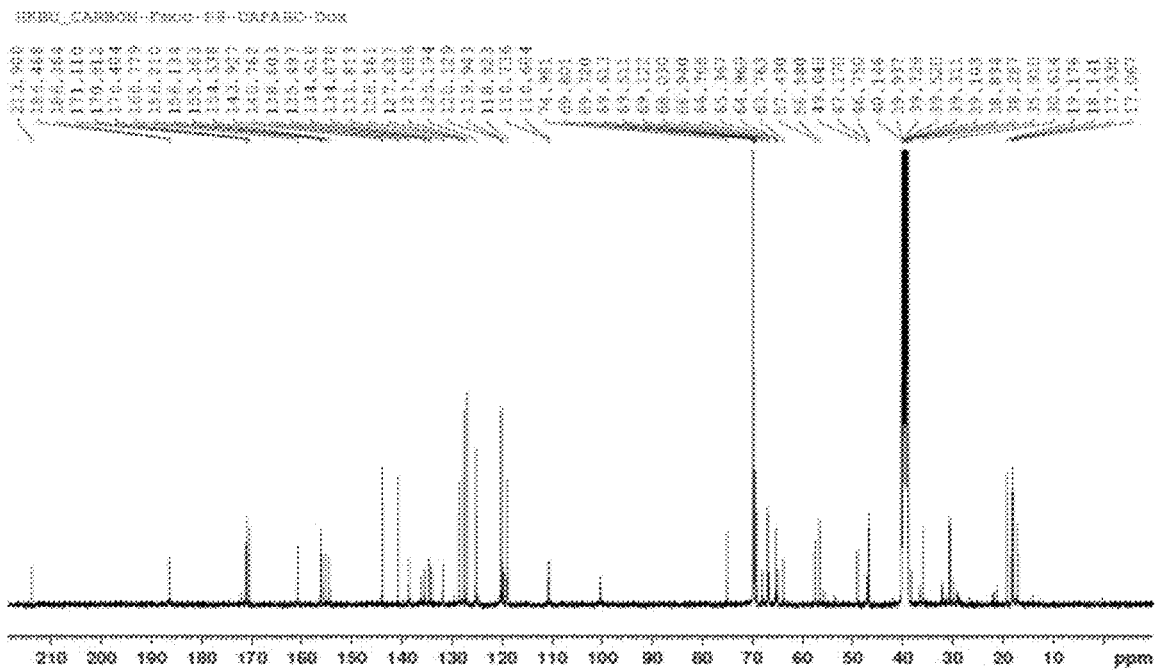
FIG. 4 is the $^{13}$C NMR spectrum of Compound 8.
Figure 5:
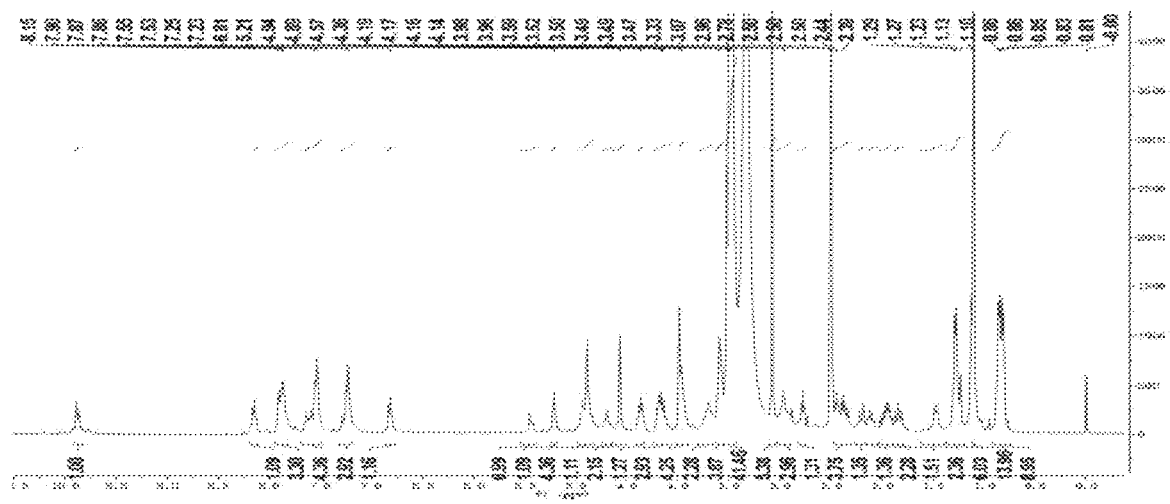
FIG. 5 is the $^1$H NMR spectrum of Compound 9.
Figure 6:
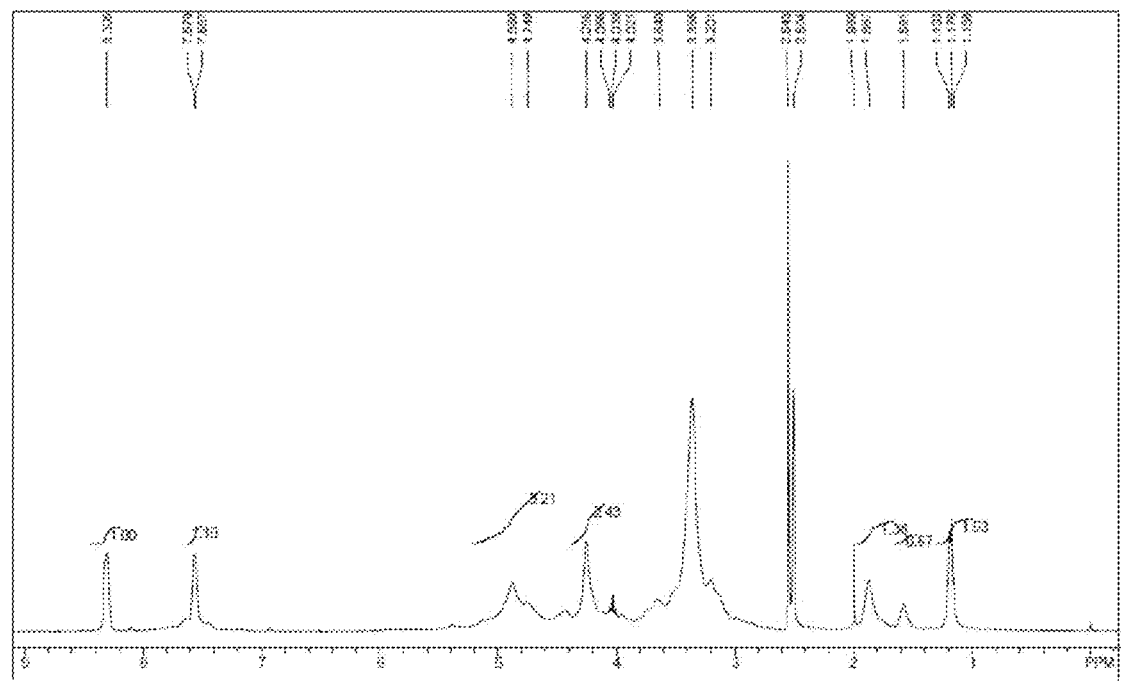
FIG. 6 is the $^1$H NMR spectrum of Compound 13.
Figure 7:
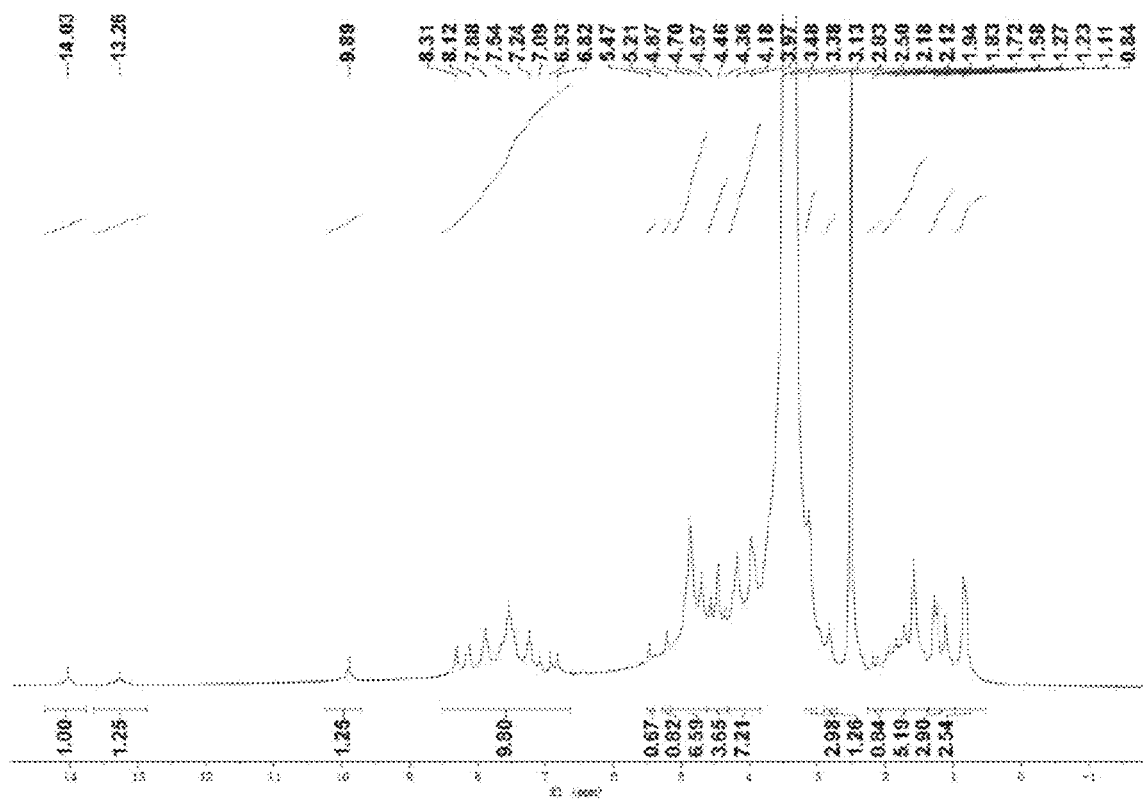
FIG. 7 is the $^1$H NMR spectrum of the final product pectin-adriamycin conjugate.

The disclosure will be further described in detail by means of the following examples, but these examples do not have any limitation effect on the disclosure.

Example 1

150 g of Compound 1 (0.44 mol) was dissolved in 1.5 L of THF, and NHS (56 g, 0.49 mol) and DCC (137 g, 0.66 mol) were added in sequence, the mixture was stirred for overnight at room temperature, and then is filtered. The solid was washed twice with dichloromethane, and the filtrate was concentrated to dry, which was recrystallized once to obtain a pure product of Compound 2.

Example 2

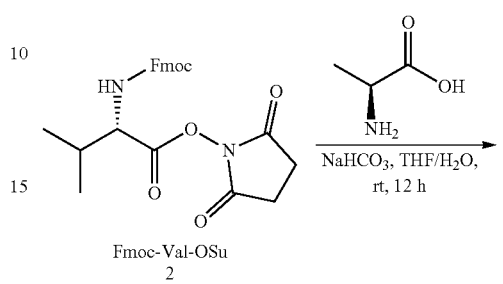

Fmoc-Val-OSu
2

Fmoc-Val-Ala-OH
3

147 g of Compound 2 (0.34 mol) was dissolved in 1.5 L of THF, and L-alanine (32 g, 0.35 mol) and NaHCO$_3$ (30 g, 0.35 mol) were added in sequence, and then 500 mL of water was added. The ratio of THF to water was adjusted so that the reaction solution became a single phase (being difficult). The reaction solution was stirred for overnight at room temperature. After the reaction was completed, the reaction solution was concentrated to remove THF, and was diluted by adding water. The pH was adjusted to 3-4 with HCl, and then a solid was precipitated out. The solid was washed with water and dried in vacuum, and then was washed with ethyl acetate to obtain 130 g of the product 3 (containing a small amount of impurities), which was purified by crystallization.

Example 3

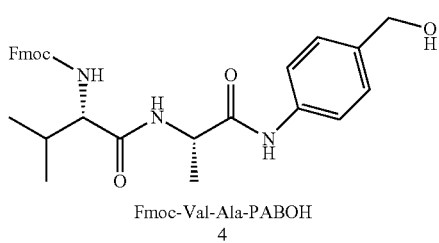

30 g of Compound 3 (73 mmol) was suspended in 500 mL of dichloromethane, then 4-aminobenzyl alcohol (11 g, 90 mmol) and EEDQ (27 g, 113 mmol) were added in sequence, and finally methanol was added until the solution was clarified. The solution was stirred for overnight at room temperature and filtered. The solid was washed with dichloromethane, and the filtrate was concentrated to dry to obtain crude Compound 4, which was washed with methyl tert-butyl ether to obtain 2.0 g of a pure product.

Example 4

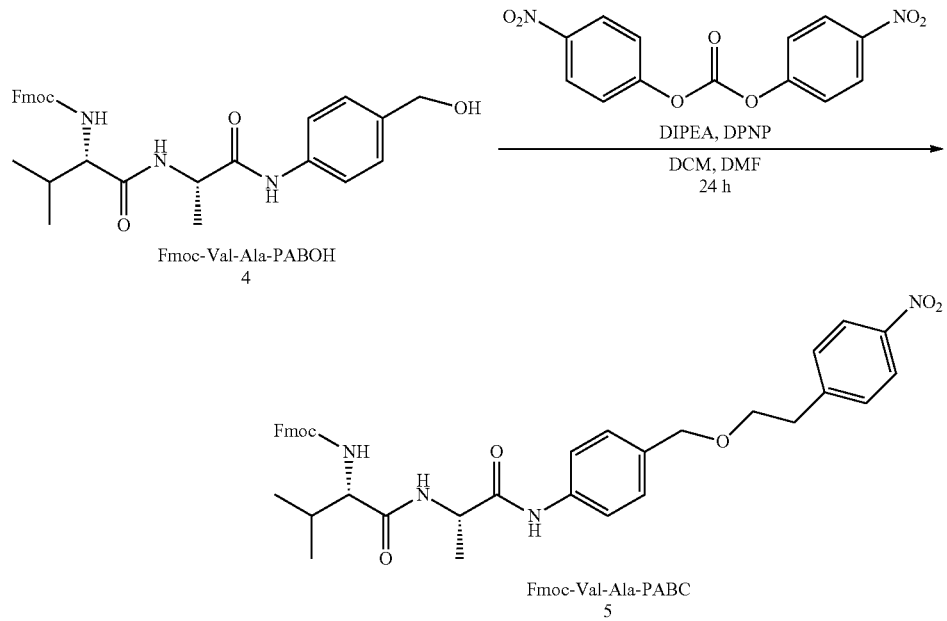

21 g of Compound 4 (41 mmol) was suspended in 500 mL of dichloromethane, then DIPEA (16 g, 126 mmol) and di(p-nitrobenzene) carbonate (18.5 g, 69 mmol) were added in sequence, and finally DMF was added until the solution was clarified. The solution was stirred for overnight at room temperature. DMF was removed by reduced pressure distillation, the viscous solid was washed with a small amount of methanol and then was recrystallized with petroleum ether and ethyl acetate (or methyl tert-butyl ether) for several times to obtain 7 g of pure Compound 5.

Example 5

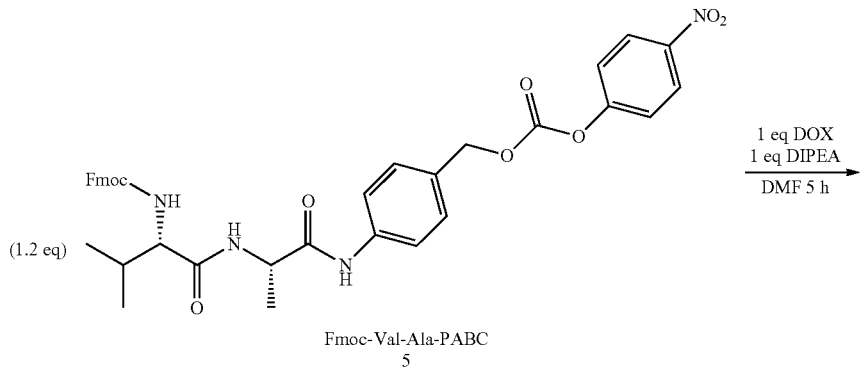

-continued

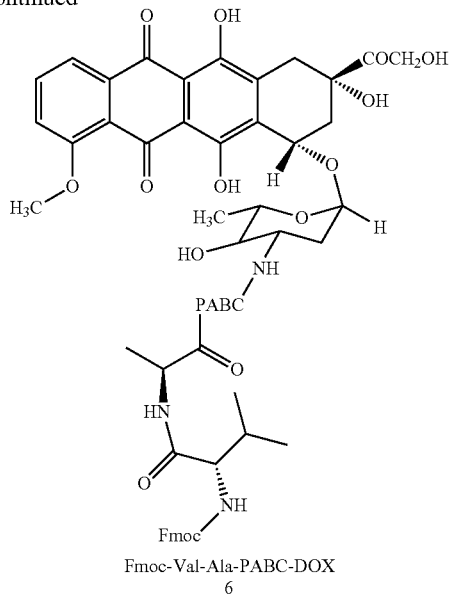

Fmoc-Val-Ala-PABC-DOX
6

690 mg of adriamycin hydrochloride and 1.036 g of Compound 5 were weighed and charged in a round-bottom flask and then 10 mL of DMF was added. 0.21 mL of DIPEA was added under stirring, and the mixture was reacted for 5 hours at room temperature. After the reaction was completed, the reaction solution was slowly dripped into methyl tert-butyl ether, and then was centrifuged to obtain a crude product, which was dissolved with a small amount of DMF for a second recrystallization to obtain 1.076 g of a product with a yield of 78%.

Example 6

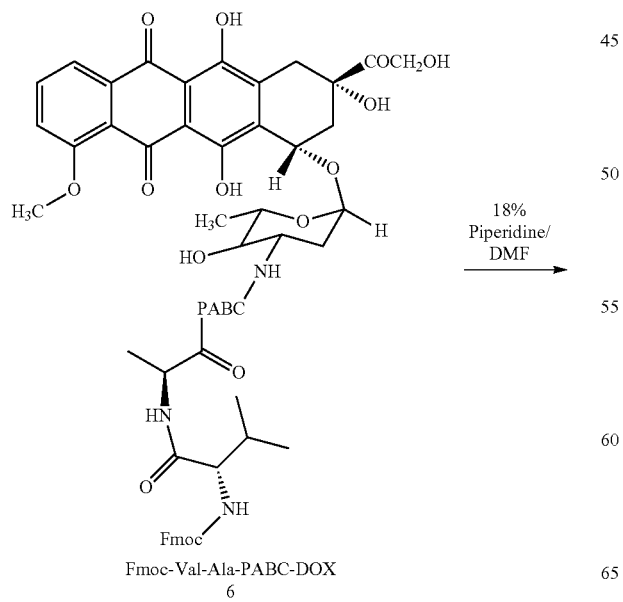

Fmoc-Val-Ala-PABC-DOX
6

18% Piperidine/ DMF
→

-continued

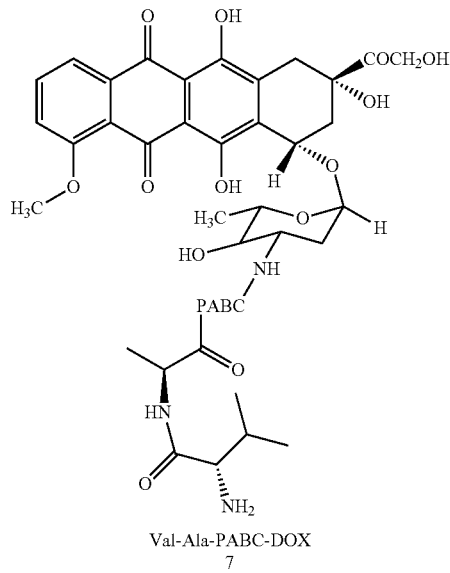

Val-Ala-PABC-DOX
7

400 mg of Compound 6 was weighed and charged in a round-bottom flask and then 10 mL of DMF was added. 1.8 mL of piperidine was added rapidly under stirring at room temperature, and the mixture was reacted at room temperature for 70 seconds. After the reaction was completed, the reaction solution was rapidly poured into methyl tert-butyl ether in an ice bath, and then was centrifuged to obtain a crude product. The crude product was dissolved with a small amount of DMF, and then was dripped slowly into methyl tert-butyl ether at room temperature for a second recrystallization to obtain 210 mg of a product with a yield of 66%.

Example 7

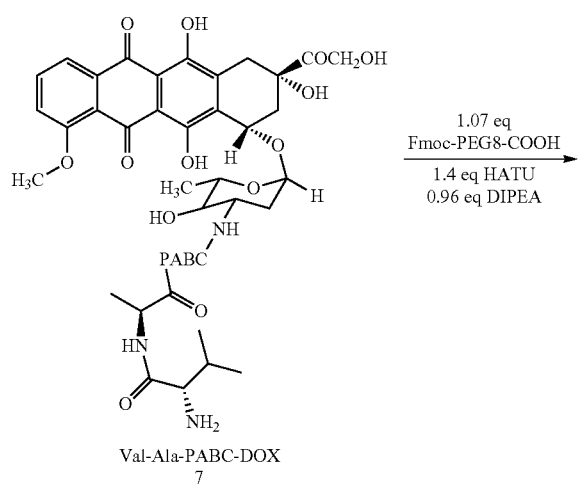

Val-Ala-PABC-DOX
7

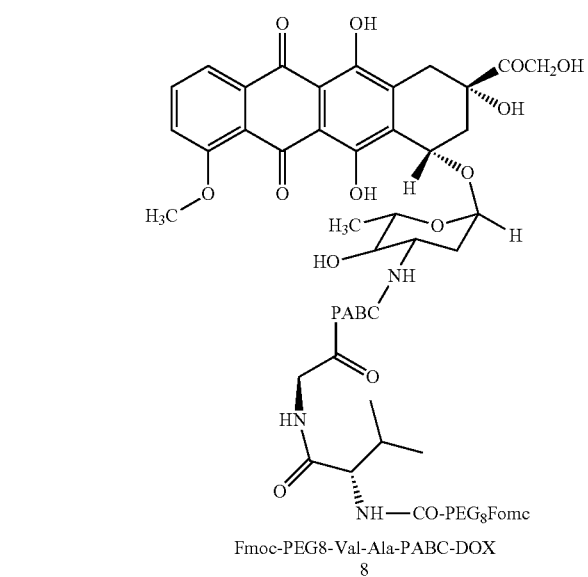

Fmoc-PEG8-Val-Ala-PABC-DOX
8

Fmoc-PEG8-COOH =

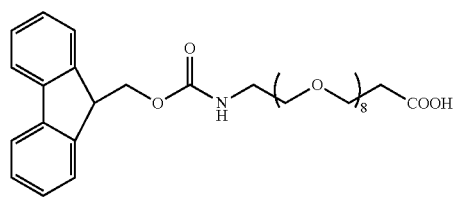

565 mg of PEG8 was weighed and charged in a round bottom flask, and then 5 mL of DMF was added. After that, 440 mg of HATU and 0.13 mL of DIPEA 0.13 were added under stirring at room temperature. Compound 7 was dissolved with a small amount of DMF, and then was added in a reaction bottle with a dropper (5 mL of solvent was used in total). The reaction solution was reacted under stirring at room temperature for 1.5 h. After the reaction was completed, the reaction solution was slowly added into methyl tert-butyl ether, and then was centrifuged to obtain a crude product. The crude product was dissolved with a small amount of DMF, and then was dripped into methyl tert-butyl ether again for a second recrystallization. Column chromatography purification was performed with Ea:MeOH=20:1. The yield was 55%.

Confirmation of Compound 8:

$^1$H NMR (400 MHz, DMSO-d6) ppm: 14.03 (s, 1H), 13.27 (s, 1H), 9.88 (s, 1H), 8.16 (d, j 1H), 7.91-7.87 (m, 5H), 7.85-7.63 (m, 3H), 7.54 (d, j=8.4 Hz, 2H), 7.51 (t, j=7.6 Hz, 3H), 7.32 (t, j 7.6 Hz, 2H), 7.24 (d, j=8.4 Hz, 2H), 6.19 (s, 1H), 5.45 (s, 1H), 5.22 (d, j=2.4 Hz, 1 h), 4.9 (m, 4H), 4.57 (s, 2H), 4.38415 (m, 8H), 4.0 (s, 3H), 3.6 (t, j 2H), 3.5-3.3 (m, 32H), 3.12 (m, 2H), 2.96 (m, 2H), 2.42 (m, 2H), 2.2 (m, 2H), 1.9 (m, 2H), 1.43 (m, 1H), 1.22 (m, 4H), 0.86 (d, j=4 Hz, 3H), 0.82 (dj=4 Hz, 3H)

$^{13}$CNMR (100 MHz, DMSO-d6) ppm: 171.11, 170.91, 170.40, 160.78, 156.21, 156.13, 155.36, 154.54, 143.93, 140.76, 128.56, 127.64, 127.09, 125.19, 120.13, 118.92, 110.60, 74.98, 69.80, 69.72, 69.61, 69.51, 69.12, 66.94, 65.37, 63.76, 57.49, 56.58, 49.05, 46.75, 35.91, 10.61, 19.18, 18.14, 17.93, 17.07.

MALDI-TOPMS: m/z 1531.2103 [(M+Na+H)+, C77H97N5O26].

RP-HPLC (Agilent 1260) 20.641 min, and the peak area: 92.4038%.

Example 8

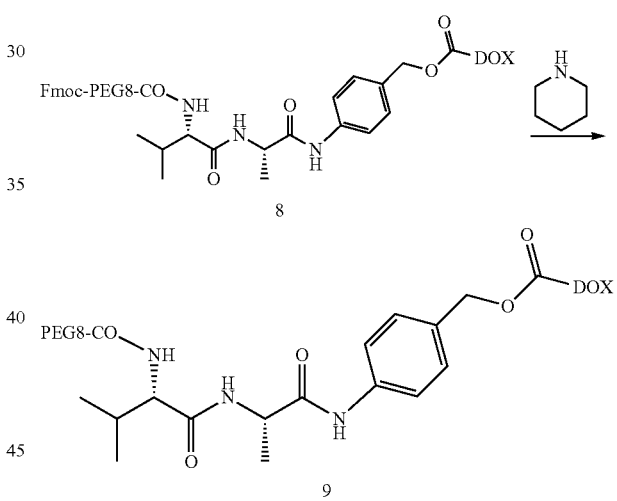

200 mg of Compound 8 was weighed and charged in a round-bottom flask, and then 6 mL of DMF was added. 660 uL of piperidine was added rapidly under stirring at room temperature, and the mixture was reacted for 140 s at room temperature. After the reaction was completed, the reaction solution was rapidly poured into methyl tert-butyl ether in an ice bath, and then was centrifuged to obtain a crude product. The crude product was dissolved with a small amount of DMF, and then was dripped slowly into methyl tert-butyl ether at room temperature for a second recrystallization.

Example 9

2 g of citrus pectin (a purchased raw material) was dissolved in 200 mL (0.2 mol/L) of a diluted nitric acid solution. The temperature was raised to 85 degree Celsius (the internal temperature was 83 degree Celsius, and the external temperature was 90 degree Celsius). When the temperature was 85 degree Celsius (the actual internal temperature was 83 degree Celsius), the timing was started. The heating was stopped after the reaction was performed for about 2 hours. After the temperature was decreased to room temperature, the reaction solution was dripped into 800 mL of anhydrous ethanol, filtered via a membrane, washed and then dried in vacuum to obtain Compound 10.

Confirmation of Compound 10:

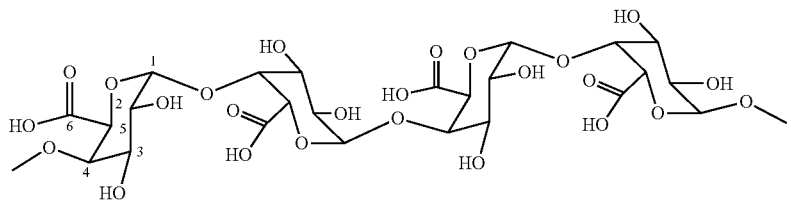

IR (KBr, v, cm$^{-1}$): 3421 (O—H), 2925 (C—H), 1740 (COOH), 1632 (COOH), 1414, 1384, 1334, 1234, 1146 (C—O—C), 1102 (C—O—C, C—OH), 1018 (C—OH), 952, 885, 831 (a-D-GalA), 742, 634.

$^1$HNMR (400 MHz, D2O) δppm: 5.10 (s, 1HH-1), 5.07 (s, 1H, H-5)) 4.50 (s, 1H, H-4), 4.05 (d, J=10.4, 1H, H-3), 3.78 (d, J=10.4, H-2).

$^{13}$CNMR (100 MHz, D2O) δppm: 172.56 (COOH), 99.86 (C-1, αtype), 78.30 (C-5), 70.34 (C-4), 68.10 (C-3), 67.91 (C-2).

$^1$HNMR (400 MHz, DMS O-d6) δppm: 12.52 (COOH, 1H), 5.01-185 (m, 3H), 4.16 (s, 1H), 3.67-3.59 (m, 3H).

$^{13}$CNMR (100 MHz, DMSO-d6) δppm: 170.44 (COOH), 98.69 (C-1, αtype), 76.71 (C-5), 69.55 (C-4), 68.24 (C-3), 67.90 (C-2).

Example 10

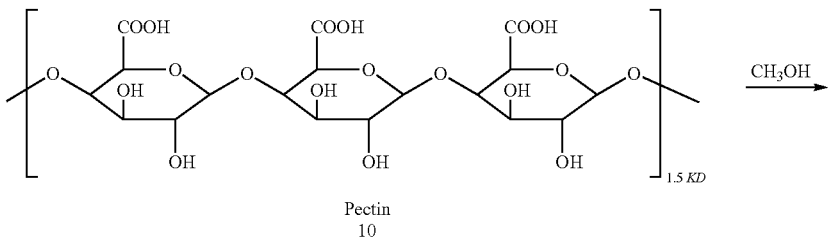

Pectin
10

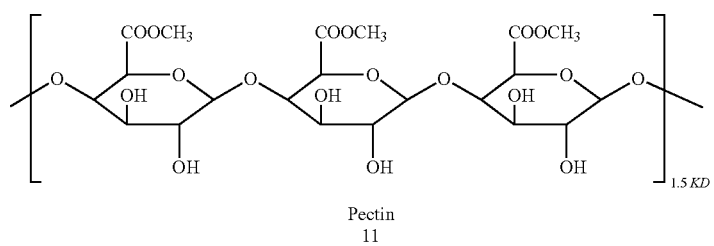

Pectin
11

2 g of Compound 10 was weighed and charged in a single neck bottle, and then 20 mL of methanol and 2 mL of concentrated HCl were added. When the internal temperature was raised to 55 degree Celsius, the timing was started. After reaction was performed for 7 hours, the stirring was stopped. Then, the temperature was decreased, and the reaction solution was dripped into anhydrous ethanol, stirred, filtered, washed and then dried in vacuum to obtain Compound 11.

Example 11

600 mg of Compound 11 was charged in a round-bottom flask, and 3.16 g of 3-amino-1-propanol (a viscous liquid) was added, and then the mixture was stirred for 2 days. After the reaction time was more than 48 hours, the clarified viscous reaction solution was slowly dripped into anhydrous ethanol, stirred, filtered and washed, and then dried in vacuum to obtain Compound 12.

Example 12

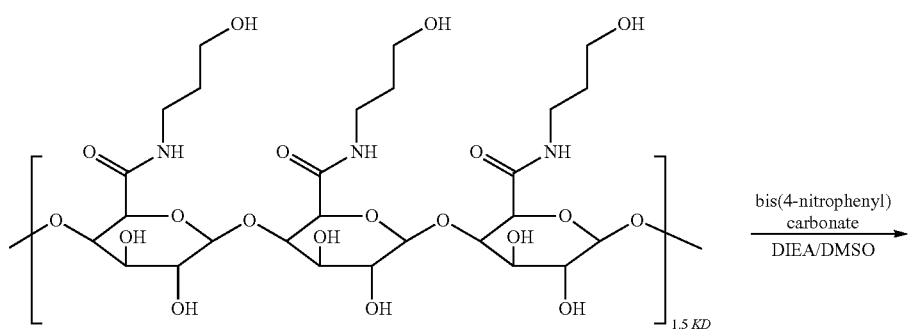

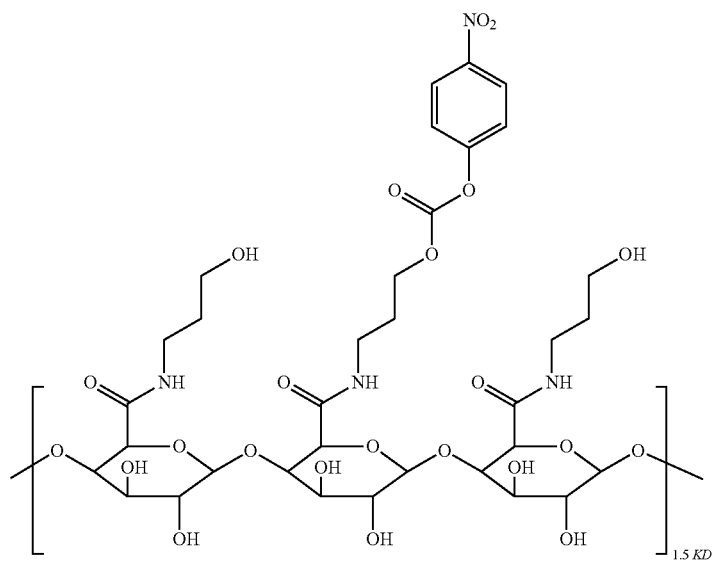

1 g of Compound 12 was weighed and dissolved sufficiently in 15 ml of DMSO, and 1.29 g of di(p-nitrophenyl) carbonate was added, then 0.7 mL of DIEA was added. The reaction was carried out for overnight (over 12 h). Finally, the reaction solution was slowly ripped into an EA solution (200 mL), filtered rapidly, washed and dried in vacuum to obtain Compound 13.

Confirmation of Compound 13:
$^1$H NMR (400 MHz, DMSO-d6) δppm: 8.305 (s, 2H), 7.56 (d, 2H), 4.88-4.79 (m), 4.26-4.02 (m), 3.64-3.20 (m), 1.98 (s, 2H), 1.58 (s, 1H), 1.19-1.16 (m).

Example 13

The Compound 13 was weighed and dissolved sufficiently in a mixed solution of DMF and DMSO, and then Compound 9 was added. After being stirred uniformly, DIEA was added to react at room temperature for 24 hours. Then the solution was directly subjected to DMSO-water gradient dialysis. HPLC detection was performed until no adriamycin or its derivative was detectable. After dialysis was completed, freeze drying was performed to obtain a pectin-adriamycin conjugate.

Confirmation of the pectin-adriamycin conjugate:
$^1$HNMR (400 MHz, DMSO-d$_6$) δppm: 14.03 (s, 1H), 13.26 (s, 1H), 9.89 (s, 1H), 8.31-6.82 (m, 10H), 5.47-3.38 (m), 1.95-0.84 (m).

Example 14

In this example, the pectin-adriamycin conjugate (obtainable from Examples 1-13) has the following structure:

The concentration of cell suspension was adjusted, and 100 uL of the cell suspension was added per well, then the cells were plated so that the density of cells to be tested was 4000 cells/well (the marginal wells being filled with a sterile PBS). Incubation was performed for 24 hours at 5% $CO_2$ and 37° C. Then the medium was discarded, and pectin-adriamycin or adriamycin with a concentration gradient (containing 0.125, 0.25, 0.5, 1.0, 2.0, 4.0, 8.0 and 16.0 ug/mL of amoxicillium) was added, and three repetitions were set for each concentration. Then incubation was performed for 48 hours in an incubator at 5% $CO_2$ and 37° C. 10 μl of a CCK-8 solution was added to each well to continue cultivation for 2 hours. The absorbance of each well at 450 nm was measured with an Enzyme-labelled meter, and IC50 values of pectin-adriamycin and adriamycin for various cancer cells were calculated.

TABLE 1

| | In-vitro cytotoxicity test | | | | |
| --- | --- | --- | --- | --- | --- |
| | HT-29 colon cancer | HepG-2 liver cancer | SMMC7721 liver cancer | SKOV3 ovarian cancer | MCF-7 breast cancer |
| Pectin-adriamycin conjugate | 10.74 ug/ml | 4.11 ug/ml | 2.31 ug/ml | 5.488 ug/ml | 3.961 ug/ml |
| Adriamycin | 10.93 ug/ml | 4.375 ug/ml | 2.618 ug/ml | 5.702 ug/ml | 3.97 ug/ml |

The results of the in-vitro cytotoxicity test shown in Table 1 showed that, there was no any significant difference in the inhibition rate of the pectin-adriamycin conjugate prepared in this disclosure for various cancer cells when compared to the positive control drug adriamycin, and had a good in-vitro cytotoxicity effect.

Example 15

As the pectin-adriamycin conjugate (obtainable from Examples 1-13) prepared in this disclosure was accumulated in the tumor tissue through the EPR effect in vivo so as to achieve the purpose of passive targeting, the in-vivo pharmacodynamic effect of the pectin-adriamycin conjugate prepared in this disclosure on tumor-bearing mice was investigated.

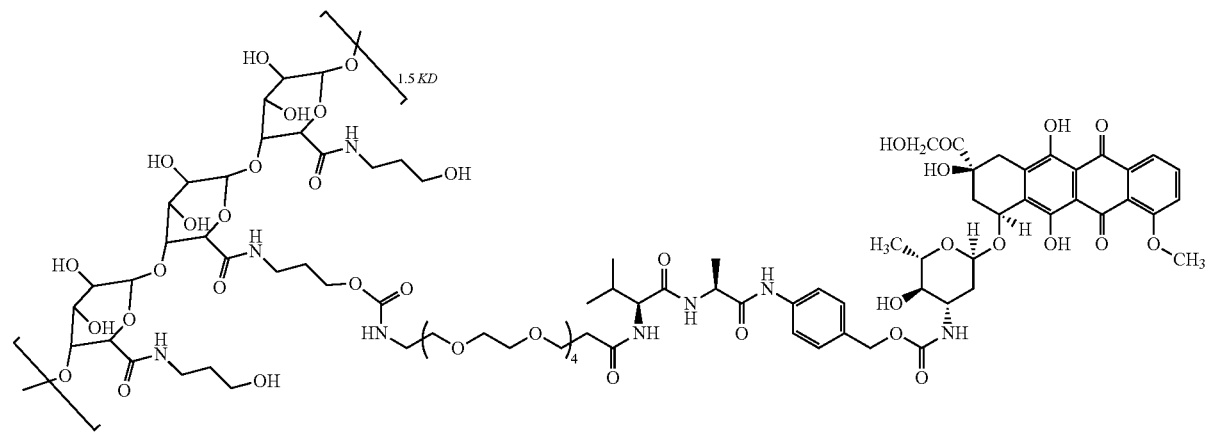

In-vitro cytotoxicity test: HT-29 colon cancer cells, HepG-2 liver cancer cells, SMMC7721 liver cancer cells, SKOV3 ovarian cancer cells and MCF-7 breast cancer cells that were growing at the logarithmic phase were collected.

In-vivo pharmacodynamic test: H22 liver cancer cells, 4T1 breast cancer cells, EMT6 breast cancer cells and HT-29 colon cancer cells that were growing at logarithmic phase were collected, and the concentration of the cell suspension was adjusted to $3\times10^7$ cells/mL. The cells were subcutaneously inoculated into right upper extremity of Balb/c mice or nude mice with 0.1 mL per mouse (containing about $3\times10^6$ cells). After the average tumor volume of the inoculated mice was reached 100 mm³, the tumor-bearing mice were randomly divided into a negative control group (with 0.9% sodium chloride injection), an adriamycin control group (5 mg/kg) and a pectin-adriamycin experimental group (the equivalent of adriamycin being 5 mg/kg) respectively, 8 mice for each group, the above various drugs were intravenously injected for 4 times in total. The tumor volume change and the body weights were recorded, and the equation for volume calculation was as follows: volume=(length×width²)/2.

In the in-vivo pharmacodynamic test, the pectin-adriamycin conjugate prepared in this disclosure had a curative effect on H22 liver cancer, 4T1 breast cancer, EMT-6 breast cancer and HT-29 colon cancer better than that of the adriamycin control. The pectin-adriamycin conjugate prepared in this disclosure could obviously inhibit the tumor growth of H22 liver cancer, 4T1 breast cancer and EMT-6 breast cancer in the tumor-bearing mice, and had higher inhibition rates, being 72.98%, 78.1% and 71.68% respectively. However, the inhibition rates of adriamycin as a control on H22 liver cancer, 4T1 breast cancer and EMT-6 breast cancer in the tumor-bearing mice were lower than those of the pectin-adriamycin conjugate prepared in this disclosure, being 53.42%, 50.61% and 56.95% respectively. In the test, the body weights of the mice in the pectin-adriamycin conjugate group prepared in this disclosure were not significantly decreased, and no mouse died. However, the body weights of the mice in the adriamycin group were significantly decreased, the body weights were decreased by more than 15%, and minormice died. The in-vivo pharmacodynamic results showed that the pectin-adriamycin conjugate prepared in this disclosure had the effect-enhancing and toxicity-reducing effects when compared to adriamycin. After H22 liver cancer tumor-bearing mice were killed, the tumor tissues were taken, and the imaging intensity of adriamycin in the tissue was observed with a small animal living body fluorescence imaging system. It was found that the tumors of the mice in the pectin-adriamycin conjugate administration group prepared in this disclosure exhibited a strong adriamycin fluorescence. This indicated that the pectin-adriamycin conjugate prepared in this disclosure was accumulated in the tumor tissue for a long time with a high concentration.

Example 16

In order to compare the curative effect of the pectin-adriamycin conjugate prepared in this disclosure (obtainable from Examples 1-13) with that of the existing control compound (pectin and adriamycin being directly bonded by an amide bond), a H22 liver cancer mode land a 4T1 breast cancer mice model were selected for comparison.

TABLE 2

Comparison of the property differences between the pectin-adriamycinconjugate prepared in this disclosure and the control compound(pectin and adriamycinbeing bonded by an amide bond)

| | Solubility in water | Injection manner |
|---|---|---|
| The pectin-adriamycin conjugate prepared in thisdisclosure (a modified pectin-PEG8-VAPABC-adriamycin) | 10 mg/ml, solubility being greatly increased | Intravenous injection |

TABLE 2-continued

Comparison of the property differences between the pectin-adriamycinconjugate prepared in this disclosure and the control compound(pectin and adriamycinbeing bonded by an amide bond)

| | Solubility in water | Injection manner |
|---|---|---|
| The control compound (pectin and adriamycinbeingbonded by anamide bond) | Hardly soluble in water, and being prepared into a nano suspension through a formulation | Intraperitoneal injection |

Figure 8:
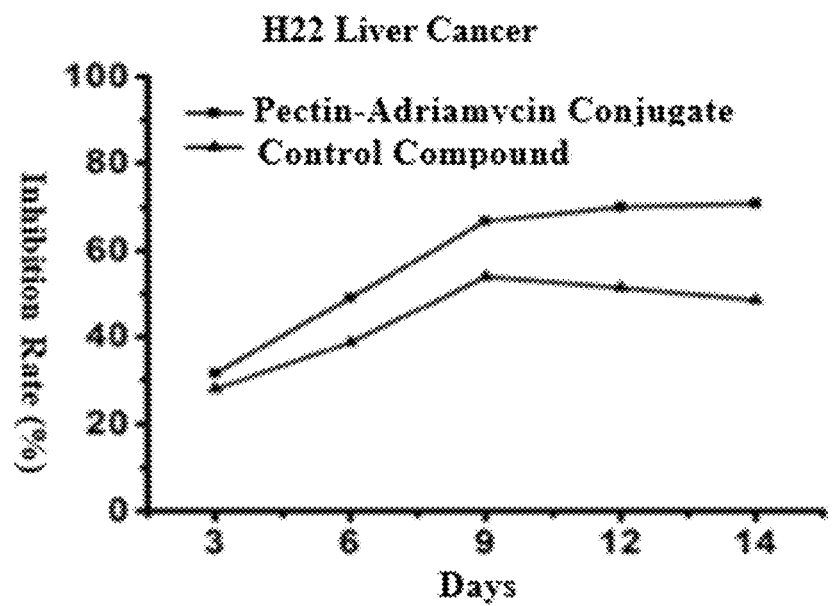
FIG. 8 shows the inhibition effect of the final product pectin-adriamycin conjugate and the control product (obtained by directly bonding pectin to adriamycin via an amide bond) on a H22 liver cancer mice tumor model.
Figure 9:
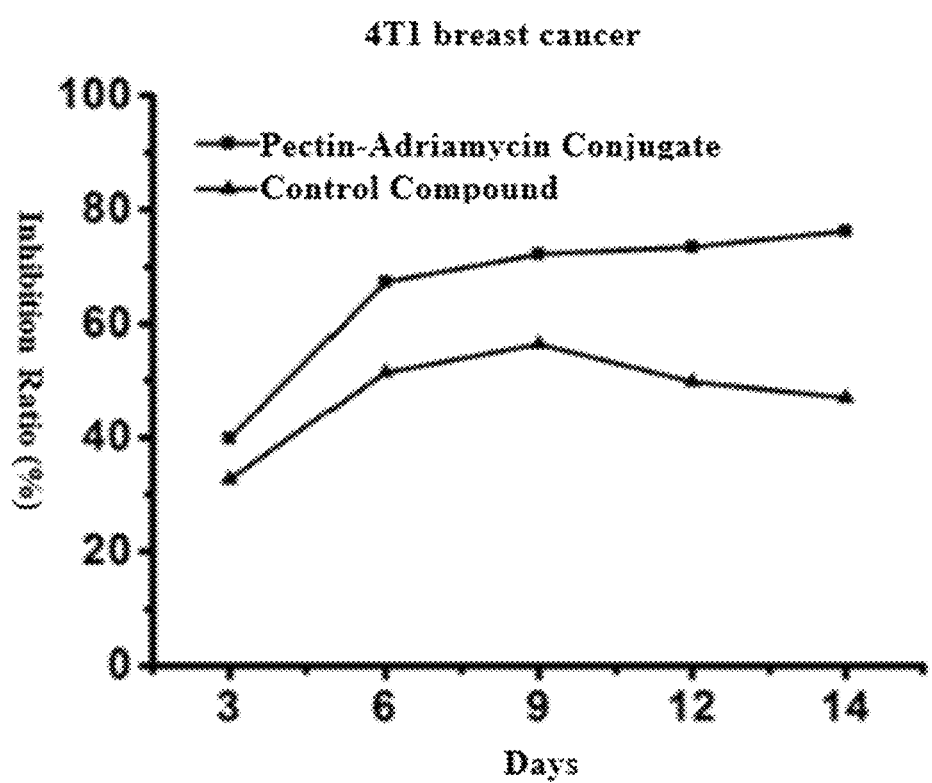
FIG. 9 shows the inhibition effect of the final product pectin-adriamycin conjugate and the control product (obtained by directly bonding pectin to adriamycin via an amide bond) on a 4T1 breast cancer mice tumor model.

The results showed that the inhibition rates of the pectin-adriamycin conjugate prepared in this disclosure on H22 liver cancer and 4T1 breast cancer mice tumor models, being 70.83% and 76.20% respectively, were obviously higher than those of the existing control compound (pectin and adriamycin being directly bonded by an amide bond), which were only 48.64% and 47.00% respectively. As shown in FIGS. 8 and 9, the present inventors have also found in the experiment that the pectin-adriamycin conjugate prepared in this disclosure not only had a higher tumor inhibition rate, but also maintained a high inhibition rate for a long time, namely under the condition that a same dosage was given, the inhibition time of the pectin-adriamycin conjugate was longer.

The above examples are used only for illustrating the technical concepts and features of this disclosure, in order that those of ordinary skill in the art can understand the contents of the disclosure and accordingly implement them, but they cannot limit the optimized protection scope of the disclosure and the synthetic routes. Any equivalent change or modification made according to the contents of the disclosure should be covered within the protection scope of the disclosure.

The invention claimed is:

1. A modified pectin-adriamycin conjugate-of the following formula:

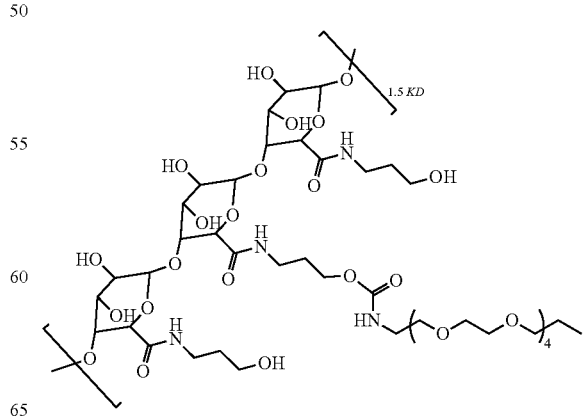

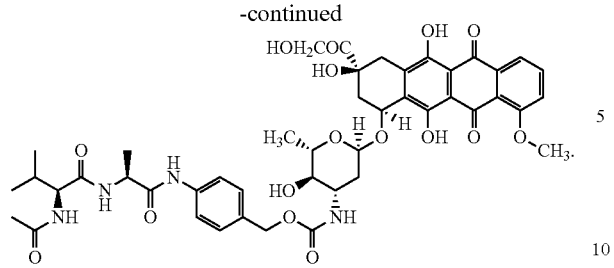
* * * * *